(12) United States Patent
Rivier et al.

(10) Patent No.: US 7,141,546 B1
(45) Date of Patent: Nov. 28, 2006

(54) CRFR2 SELECTIVE LIGANDS

(75) Inventors: Jean E. F. Rivier, La Jolla, CA (US); Wylie W. Vale, LaJolla, CA (US); Marilyn H. Perrin, LaJolla, CA (US); Jozsef Gulyas, Julian, CA (US); Dean A. Kirby, San Diego, CA (US)

(73) Assignee: The Salk Institute for Biologicial Studies, LaJolla, CA (US)

( * ) Notice: Subject to any disclaimer, the term of this patent is extended or adjusted under 35 U.S.C. 154(b) by 709 days.

(21) Appl. No.: 10/210,889

(22) Filed: Jul. 31, 2002

Related U.S. Application Data

(60) Provisional application No. 60/309,505, filed on Aug. 1, 2001.

(51) Int. Cl.
*A61K 38/16* (2006.01)
*C07K 14/00* (2006.01)

(52) U.S. Cl. .................. 514/12; 514/2; 514/9; 514/11; 530/300; 530/317; 530/324

(58) Field of Classification Search ............ None
See application file for complete search history.

(56) References Cited

U.S. PATENT DOCUMENTS

| | | | |
|---|---|---|---|
| 4,489,163 A | 12/1984 | Rivier et al. | 436/86 |
| 4,605,642 A | 8/1986 | Rivier et al. | 514/12 |
| 5,109,111 A * | 4/1992 | Rivier et al. | 530/306 |
| 5,235,036 A * | 8/1993 | Kornreich et al. | 530/306 |
| 5,245,009 A * | 9/1993 | Kornreich et al. | 530/306 |
| 5,493,006 A | 2/1996 | de Miranda et al. | 530/306 |
| 5,510,458 A * | 4/1996 | Kornreich et al. | 530/306 |
| 5,777,073 A | 7/1998 | Rivier | 530/306 |
| 5,874,227 A | 2/1999 | Rivier | 435/7.1 |
| 6,214,797 B1 | 4/2001 | Vale, Jr. et al. | 514/12 |

OTHER PUBLICATIONS

A.J. Miles, et al. J. Biol. Chem. (1994) 269(49), pp. 30939-30945.*
CRISP Thesaurus. http://crisp.cit.nih.gov/Thesaurus/index.htm, accessed Jan. 31, 2006, 4 pages.*
Bonk, I. et al., Development of a Selective Photoactivatable Antagonist for Corticotropin-Releasing Factor Receptor, Type 2 ($CRF_2$), *Eur. J. Biochem* (2002) 269, 5288-5294.
Lawrence, A.J. et al., The Highly Selective $CRF_2$ Receptor Antagonist K41498 Binds to Presynaptic $CRF_2$ Receptors in Rat Brain, *British Journal of Pharmacology* (2002) 136, 895-904.
Ruhmann, A. et al., Structural Requirements for Peptidic Antagonists of the Corticotropin-Releasing Factor Receptor (CRFR): Development of $CRF_2$ β-Selective Antisauvagine-30 P.N.A.S. (Dec. 1998) 95, 15624-15269.

* cited by examiner

*Primary Examiner*—Cecilia J. Tsang
*Assistant Examiner*—Andrew D. Kosar
(74) *Attorney, Agent, or Firm*—Fitch, Even, Tabin & Flannery

(57) ABSTRACT

CRF peptide analogs that bind to CRFR2 with an affinity far greater than they bind to CRFR1. These analogs exhibit CRF antagonist activity, and they can be based upon the native structures of sauvagine, CRF, and urocortin.

20 Claims, No Drawings

CRFR2 SELECTIVE LIGANDS

This application claims priority from Provisional Application No. 60/309,505, filed Aug. 1, 2001, the disclosure of which is incorporated herein by reference.

This invention was made with Government support under grants numbers PO1-DK-26741 and DK-41301, awarded by the National Institutes of Health. The Government has certain rights in this invention.

This invention is generally directed to peptides and to the pharmaceutical treatment of mammals using such peptides. More specifically, the invention relates to analogs of the hentetracontapeptide CRF which are selective to one family of CRF receptors, to pharmaceutical compositions containing such CRF analogs, to methods of treatment of mammals using such CRF analogs, and to methods of screening for new drugs using such peptides.

BACKGROUND OF THE INVENTION

Ovine CRF (oCRF) was characterized in 1981 as a 41-residue amidated peptide. oCRF lowers blood pressure in mammals when injected peripherally and stimulates the secretion of ACTH and β-endorphin. Rat CRF (rCRF) was later isolated, purified and characterized; it was found to be a homologous, amidated hentetracontapeptide as described in U.S. Pat. No. 4,489,163, the disclosure of which is incorporated herein by reference. The amino acid sequence of human CRF (hCRF) has now been determined to be the same as that of rCRF.

In about 1981, a 40-residue amidated peptide was isolated from the skin of the South American frog *Phyllomedusa sauvagei* and referred to as sauvagine. It was characterized by Erspamer et al. and was described in *Regulatory Peptides*, Vol. 2 (1981), pp. 1–13. When given intravenously (iv), sauvagine and oCRF have been reported to cause vasodilation of the mesenteric arteries so as to lower blood pressure in mammals and also in stimulating the secretion of ACTH and β-endorphin. However, when administered intracerebroventricularly (icv), there is an elevation of heart rate and mean arterial blood pressure, which are secondary to activation of the sympathetic nervous system.

Although originally isolated and characterized on the basis of its role in this hypothalamopituitary-adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the likely involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the hypothalamic-pituitary-adrenal, CRF has also been shown to modulate autonomic and behavioral changes, some of which occur during the stress response. Many of these behavioral changes have been shown to occur independently of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF or a CRF analog fails to affect certain of these changes, it appears that CRF exhibits a direct brain action with respect to such functions, which include appetite suppression, increased arousal and learning ability. However, CRF antagonists given peripherally attenuate stress-mediated increases in ACTH secretion, and when delivered into the cerebral ventricles can mitigate stress-induced changes in autonomic activity and behavior.

As a result of the extensive anatomical distribution and multiple biological actions of CRF, this regulatory peptide is believed to be involved in the regulation of numerous biological processes. CRF has also been implicated in the regulation of inflammatory responses. Although it has been observed that CRF plays a pro-inflammatory role in certain animal models, CRF appears to suppress inflammation in others by reducing injury-induced increases in vascular permeability.

CRF analogs are generally effective in the prophylaxis and/or treatment of stress-related illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; cancer; infertility; muscular spasms; urinary incontinence; hypoglycemia and immune dysfunctions including stress induced immune dysfunctions, immune suppression and human immunodeficiency virus infections; and stress-induced infections in humans and animals.

CRF antagonists containing D-isomers of α-amino acids were developed, such as those shown in U.S. Pat. No. 5,109,111. Antagonists of CRF are disclosed in U.S. Pat. No. 4,605,642, issued Aug. 12, 1986, the disclosure of which is incorporated herein by reference. Cyclic CRF antagonists exhibiting biopotency were later developed as disclosed in U.S. Pat. Nos. 5,493,006, 5,510,458, 5,777,073 and 5,874,227.

Recent clinical data have implicated corticotropin-releasing factor ("CRF") in neuropsychiatric disorders and in neurodegenerative diseases, such as Alzeimer's disease. Alzheimer's disease is a neurodegenerative brain disorder which leads to progressive memory loss and dementia. By current estimates, over two million individuals in the United States suffer from this disease. In particular, several lines of evidence have implicated CRF in Alzheimer's disease (AD) (Behan et al., Nature 378(16):284, 1995). First, there are dramatic (greater than 50%) decreases in CRF (Bissette et al., JAMA 254:3067, 1985; DeSouza et al., Brain Research 397:401, 1986; Whitehouse et al., Neurology 37:905, 1987; DeSouza, Hospital Practice 23:59, 1988; Nemeroff et al., Regul. Peptides 25:123, 1989) and reciprocal increases in CRF receptors (DeSouza et al., 1986; DeSouza, 1988) in cerebrocortical areas that are affected in AD, while neither CRF nor CRF receptors are quantitatively changed in non-affected areas of the cortex (DeSouza et al., 1986). Second, chemical affinity crosslinking studies indicate that the increased CRF receptor population in cerebral cortex in AD have normal biochemical properties (Grigoriadis et al., Neuropharmacology 28:761, 1989). Additionally, observations of decreased concentrations of CRF in the cerebrospinal fluid (Mouradian et al., Neural Peptides 8:393, 1986; May et al., Neurology 37:535, 1987) are significantly correlated with the global neuropsychological impairment ratings, suggesting that greater cognitive impairment is associated with lower CRF concentrations in cerebrospinal fluid (Pomara et al., Biological Psychiatry 6:500, 1989).

Available therapies for the treatment of dementia are severely limited. Tacrine™, a recently approved drug, leads to only marginal memory improvement in Alzheimer's patients, and has the undesirable side effect of elevating liver enzymes. Alterations in brain CRF content have also been found in Parkinson's disease and progressive supranuclear palsy, neurological disorders that share certain clinical and pathological features with AD. In cases of Parkinson's disease, CRF content is decreased and shows a staining pattern similar to cases of AD (Whitehouse et al., 1987; DeSouza, 1988). In progressive supranuclear palsy, CRF is decreased to approximately 50% of control values in frontal, temporal, and occipital lobes (Whitehouse et al., 1987; DeSouza, 1988).

Some depressive disorders are also associated with decreased levels of CRF. Patients in the depressive state of seasonal depression and in the period of fatigue in chronic fatigue syndrome demonstrate lower levels of CRF in the cerebrospinal fluid (Vanderpool et al., J. Clin. Endocrinol. Metab. 73:1224, 1991). Although some depressions have a high improvement rate and many are eventually self-limiting, there are major differences in the rate at which patients recover. A major goal of therapy is to decrease the intensity of symptoms and hasten the rate of recovery for this type of depression, as well as preventing relapse and recurrence. Anti-depressants are typically administered, but severe side effects may result (e.g., suicidality with fluoxetine, convulsions with bupropion). (See Klerman et al. in Clinical Evaluation of Psychotropic Drugs: Principles and Guidelines, R. F. Prien and D. S. Robinson (eds.), Raven Press, Ltd. N.Y., 1994, p. 281.)

Hypoactivation of the stress system as manifested by low CRF levels may play a role in other disorders as well. For examples, some forms of obesity are characterized by a hypoactive hypothalamic-pituitary-adrenal axis (Kopelman et al., Clin. Endocrinol (Oxford) 28:15, 1988; Bernini et al., Horm. Res. 31:133, 1989), some patients with post-traumatic stress syndrome have low cortisol excretion (Mason et al., J. Neu. Men. Dis. 174:145, 1986), and patients undergoing withdrawal from smoking have decreased excretion of adrenaline and noradrenaline, as well as decreased amounts of cortisol in blood (West et al., Psychopharmacology 84:141, 1984; Puddy et al., Clin. Exp. Pharmacol. Physiol. 11:423, 1984). These manifestations all point to a central role for CRF in these disorders because CRF is the major regulator of the hypothalamic-pituitary-adrenal axis. Treatments for these disorders have poor efficacy. For example, the most effective approach to treatment of obesity is a behavior-change program. However, few participants reach goal weight and the relapse rate is high (see Halmi et al. in Clinical Evaluation of Psychotropic Drugs: Principles and Guidelines, R. F. Prien and D. S. Robinson (eds.), Raven Press, Ltd. New York, 1994, p. 547).

In view of the deficiencies in treatments for such disorders and diseases, more effective treatments are needed. The present invention exploits the correlation of reduced levels of CRF with various neuro-physiologically based disorders and diseases to effectively treat such diseases by increasing levels of free CRF, and further provides other related advantages. Because these actions are mediated by CRFR2, CRFR2-selective analogs are preferred over non-selective analogs due to the possible side effects resulting from activation of other CRF receptors.

The physiological actions of CRF are mediated through activation of at least two high affinity receptors, CRFR1 and CRFR2, which are members of the seven-transmembrane family of receptors [Chen R., et al, P.N.A.S., 90:8967–8971 (1993), Perrin, M., et al., P.N.A.S, 92:2969–2973 (1995), Lovenberg, T., et al., P.N.A.S., 92:836–840 (1995), K. D. Dieterich et al. Exp. Clin. Endocrinol. Diabetes (1997) 105:65–82 and J. Spiess et al. Trends Endocrinol. Metab. (1998) 9:140–145]. Evidence from transgenic knockouts [A. Contarino et al., Brain Res. (1999) 835:1–9, G. W. Smith et al., Neuron (1998) 20:1093–1102 and P. Timpl et al., Nature Genet. (1998) 19:162–166], antisense oligonucleotide studies [S. C. Heinrichs et al., Regul. Pept. (1997) 71:15–21, G. Liebsch et al., J. Psychiatric Res. (1999) 33:153–163 and T. Skutella et al., Neuroscience (1998) 85: 795–805] and CRFR1 receptor antagonists [K. E. Habib et al., Proc. Natl. Acad. Sci. USA (2000) 97:6079–6084., J. Lundkvist et al., Eur. J. Pharmacol. (1996) 309:195–200., R. S. Mansbach et al., Eur. J. Pharmacol. (1997) 323:21–26 and S.C. Weninger et al., Proc. Natl. Acad. Sci. USA (1999) 96:8283–8288] provide evidence for the involvement of CRFR1 receptors in mediating the anxiogenic effects of CRF.

A human CRF receptor was the first to be reported, and it was cloned from a human Cushing pituitary tumor as described in Chen R., et al, P.N.A.S., 90, 8967–8971 (October 1993). It is referred to as hCRFR1 or hCRF-RA and has 415 amino acids; a splice variant thereof includes an insert of 29-amino acids. A rat CRF receptor was isolated, approximately contemporaneously, by hybridization from a rat brain cDNA library. It is referred to as rCRFR1; it also has a 415 amino acid sequence and was disclosed in Perrin, M., et al., Endocrinology, 133, 3058–3061 (1993). It was found to be 97% identical at the amino acid level to the human CRFR1, differing by only 12 amino acids. The receptor has since been reported to be widely distributed throughout the brain and the pituitary and to be likely present in the adrenals and spleen. CRF(1) receptors (CRFR1) have been relatively well characterized, and antagonists to this receptor effectively block stress-induced behaviors in rodents.

The CRFR2 receptor was identified more recently [T. Kishimoto et al., Proc. Natl. Acad. Sci. USA (1995) 92:1108–1112, W. A. Kostich et al., Mol. Endocrinol. (1998) 12:1077–1085, T. W. Lovenberg et al., Proc. Natl. Acad. Sci. USA (1995) 92:836–840. and M. Perrin et al., Proc. Natl. Acad. Sci. USA (1995) 92:2969–2973.] and exists as at least three splice variants. CRFR1 and CRFR2 receptor subtypes are 70% homologous in their amino acid sequences but appear to be pharmacologically [D. P. Behan et al., Mol. Psychiatry (1996) 1:265–277. and K. D. Dieterich et al., Exp. Clin. Endocrinol. Diabetes (1997) 105:65–82.] and anatomically distinct [D. T. Chalmers et al., J. Neurosci. (1995) 15:6340–6350. and D. H. Rominger et al., J. Pharmacol. Exp. Ther. (1998) 286:459–468]. The CRFR2 isoform is highly expressed in limbic brain regions and in the hypothalamus, suggesting possible roles in anxiety, depression and appetite control. The abundance of CRFR2 protein and mRNA in the lateral septum [D. T. Chalmers et al., *J. Neurosci.* (1995) 15:6340–6350 and D. H. Rominger et al., *J. Pharmacol. Exp. Ther.* (1998) 286:459–468], and the central role of septum in limbic brain circuitry, mediating emotional responses such as fear, anxiety and aggression [J. Menard and D. Treit, *Physiol. Behav.* (1996) 60:845–853. and E. Yadin et al., *Physiol. Behav.* (1993) 53:1077–1083].

CRFR1 is distributed throughout the brain and the sensory and motor relay sites, whereas CRFR2 is expressed in regions of the body where there is little or no expression of CRFR1, such as peripheral sites, e.g. the blood vessels, the heart, the GI tract, the lungs and the skin. In addition, while CRFR1 expression is very high in neocortical, cerebellar, and sensory relay structures, CRFR2 expression is generally confined to subcortical structures. The highest levels of CRFR2 mRNA in brain are evident within the lateral septal nucleus, the ventromedial hypothalamic nucleus and the choroid plexus. Moderate levels of CRFR2 expression are also evident in the olfactory bulb, amygdaloid nuclei, the paraventricular and supraoptic nuclei of the hypothalamus, the inferior colliculus and 5-HT-associated raphe nuclei of the midbrain. CRFR2-expressing cells are also evident in the bed nucleus of the stria terminalis, the hippocampal formation and anterior and lateral hypothalamic areas. In addition, CRFR2 receptor mRNA is also found in cerebral arterioles throughout the brain. Within the pituitary gland, CRFR2 mRNA is detectable at low levels in scattered cells while CRFR1 mRNA is readily detectable in anterior and intermediate lobes.

This heterogeneous distribution of CRFR1 and CRFR2 mRNA suggests distinctive functional roles for each receptor in CRF-related systems. The CRFR1 may be regarded as the primary neuroendocrine pituitary CRF receptor and important in cortical, cerebellar and sensory roles of CRF. The anatomical distribution of CRFR2 mRNA indicates a role for this novel receptor in hypothalamic neuroendocrine, autonomic and general behavioral actions of central CRF. The location of CRFR2, which are highly expressed in limbic brain regions, supports the involvement of these receptors in fear-conditioning (Ho et al., Brain Res Mol Brain Res (2001) 89(1–2):29–40). Additional studies to determine the effects of simultaneous inhibition of both receptor subtypes show that rats receiving both CRFR2 antisense oligonucleotide and CRFR1 antagonist froze significantly less than animals treated with either agent alone. These results provide additional evidence for the role of CRFR2 in mediating the stress-induced actions of endogenous CRF. CRFR2 is also involved in central autonomic and appetitive control. CRFR2 exists as three splice variants of the same gene and have been designated CRFR2a, CRFR2b and CRFR2g. CRFR2b is used interchangeably with CRFR2β. The pharmacology and localization of all of these proteins in brain has been well established. The CRFR1 subtype is localized primarily to cortical and cerebellar regions while the CRFR2a is localized to subcortical regions including the lateral septum, and paraventricular and ventromedial nuclei of the hypothalamus. The CRFR2b is primarily localized to heart, skeletal muscle and in the brain, to cerebral arterioles and choroid plexus. The CRFR2g has most recently been identified in human amygdala.

Both CRFR1 and CRFR2 were found in the pituitary and throughout the neocortex (especially, in prefrontal, cingulate, striate, and insular cortices), amygdala, and hippocampal formation of primates. In primates, both CRFR1 and CRFR2 may be involved in mediating the effects of CRF on cognition, behavior, and pituitary-adrenal function. The presence of CRFR1 (but not CRFR2) within the locus coeruleus, cerebellar cortex, nucleus of the solitary tract, thalamus, and striatum and of CRFR2 (but not CRFR1) in the choroid plexus, certain hypothalamic nuclei, the nucleus prepositus, and the nucleus of the stria terminalis suggests that each receptor subtype also may have distinct functional roles within the primate central nervous system. See, e.g., Sanchez et al., J. Comp. Neurol. 408:365–377.

CRF has been widely implicated as playing a major role in modulating the endocrine, autonomic, behavioral and immune responses to stress. The recent cloning of multiple receptors for CRF as well as the discovery of non-peptide receptor antagonists for CRF receptors have begun a new era of CRF study. Presently, there are five distinct targets for CRF with unique cDNA sequences, pharmacology and localization. These fall into three distinct classes, encoded by three different genes and have been termed CRFR1 and CRFR2 (belonging to the superfamily of G-protein coupled receptors) and CRF-binding protein. Expression of these receptors in mammalian cell lines has made possible the identification of non-peptide, high affinity, selective receptor antagonists. While the natural mammalian ligands oCRF and r/hCRF have high affinity for the CRFR1 subtype, they have lower affinity for the CRFR2 family making them ineffective labels for CRFR2. [$^{125}$I]Sauvagine has been characterized as a high affinity ligand for both CRFR1 and the CRFR2 subtypes and has been used in both radioligand binding and receptor autoradiographic studies as a tool to aid in the discovery of selective small molecule receptor antagonists. A number of non-peptide CRFR1 antagonists that can specifically and selectively block the CRFR1 receptor subtype have recently been identified. Compounds such as CP 154,526, NBI 27914 and Antalarmin inhibit CRF-stimulation of cAMP or CRF-stimulated ACTH release from cultured rat anterior pituitary cells. Furthermore, when administered peripherally, these compounds compete for ex vivo [$^{125}$I]sauvagine binding to CRFR1 in brain sections demonstrating their ability to cross the blood-brain-barrier. In in vivo studies, peripheral administration of these compounds attenuate stress-induced elevations in plasma ACTH levels in rats demonstrating that CRFR1 can be blocked in the periphery. Furthermore, peripherally administered CRFR1 antagonists have also been demonstrated to inhibit CRF-induced seizure activity. These data clearly demonstrate that non-peptide CRFR1 antagonists, when administered systemically, can specifically block central CRFR1 and provide tools that can be used to determine the role of CRFR1 in various neuropsychiatric and neurodegenerative disorders. In addition, these molecules will prove useful in the discovery and development of potential orally active therapeutics for these disorders. McCarthy et al., Curr Pharm Des. (1999) 5(5):289–315.

Because the CRFR1 control different functions than the CRFR2, it would be valuable to be able to regulate one family of receptors without significantly affecting the other family. oCRF and rCRF bind substantially similarly to both CRFR1 and CRFR2 families. A. Ruhmann et al. *P.N.A.S.*, 95, 15264–15269 (December 1998) reported that [D-Phe$^{11}$, His$^{12}$]-sauvagine (11–40) was an antagonist that acted selectively with respect to CRFR2β and exhibited competitive antagonism equal to about 30% of that of the then best antagonist for CRFR1 and close to equal antagonism for CRFR2β compared to this previously best reported compound. Thereafter, the search has continued for CRF analogs that will serve as effective competitive antagonists to modulate the activation of CRFR2 while having even less effect upon CRFR1.

SUMMARY OF THE INVENTION

A class of such CRF analogs has now been found that are ligands for CRFR2; these ligands are selective for CRFR2 and provide particularly potent antagonists. These peptides may be based upon a formula of sauvagine (Svg) or upon the formula of urocortin (Ucn) and may preferably have a cyclizing bond between the residues that correspond to residues 31 and 34 of the native molecule, which cyclizing bond is preferably an amide linkage between side chains of the amino acid residues in those positions. They may similarly be based upon the formula of the 41-residue peptide r/hCRF by substitution in the corresponding residues in positions 32 and 35. The C-terminus of the molecules is the native amide; however the N-terminus is preferably shortened by elimination of the first 10 residues and by acylation of a D-isomer substituent that now appears in position 11 at the N-terminus. Ligands extended by 3 residues at the N-terminus retain favorable selectivity. The comparable linear peptides also show selectivity and high binding strength to the CRFR2; however, they may not be as effective in exhibiting competitive antagonism.

Because the CRF receptor ligands of the present invention demonstrate activity at the CRFR2 receptor site, they may be used as therapeutic agents for the treatment of a wide range of disorders or illnesses including endocrine, psychiatric, and neurologic disorders or illnesses. More specifically, the CRFR2 ligands of the present invention may be useful in treating physiological conditions or disorders arising from the hypersecretion or hyposecretion of CRF. Because CRF is believed to be a pivotal neurotransmitter that activates and coordinates the endocrine, behavioral and automatic responses to stress, the CRF receptor ligands of the present invention can be used to treat neuropsychiatric disorders. Neuropsychiatric disorders which may be treatable by the CRF receptor ligands of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF analogs may also be useful in treating stress-induced immune suppression associated with various diseases states, as well as stroke. Other uses of the CRF analogs of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor ligands are disclosed. For the purposes of administration, the compounds of the present invention may be formulated as pharmaceutical compositions. Pharmaceutical compositions of the present invention comprise a CRF receptor ligand of the present invention and a pharmaceutically acceptable carrier and/or diluent. The CRF receptor ligand should be present in the composition in an amount which is effective to treat a particular disorder, that is, in an amount sufficient to achieve desired CRF receptor ligand activity, and preferably with acceptable toxicity to the patient. Preferably, the pharmaceutical compositions of the present invention may include a CRF receptor ligand in an amount from 0.1 mg to 250 mg per dosage depending upon the route of administration, and more preferably from 1 mg to 60 mg. Appropriate concentrations and dosages can be readily determined by one skilled in the art.

Such pharmaceutical formulations are facilitated because of the high solubility of these peptides at physiological pH. The administration of such CRFR2 ligands or pharmaceutically acceptable addition salts thereof to mammals, particularly humans, in accordance with the invention may be carried out to increase intestinal motility, e.g. following stress or surgery, or for the treatment of ilies or diseases resulting in gastric or esophageal reflux. They may also be used to increase angiogenesis and to combat vascular disease as well as to mitigate a positive isotropic effect that might otherwise result in congestive heart failure. Furthermore, they are useful in treating migraines by reducing vasodilation and blood flow to the brain.

In another embodiment, the present invention provides a method for treating a variety of disorders or illnesses, including endocrine, psychiatric and neurologic disorders or illnesses. Such methods include administering of a compound of the present invention to an animal in an amount sufficient to treat the disorder or illness. Such methods include systemic administration of a CRF receptor ligand of this invention, preferably in the form of a pharmaceutical composition. As used herein, systemic administration includes oral and parenteral methods of administration.

The peptides also provide the basis for valuable methods for drug screening for even more potent molecules which bind to and/or activate CRF receptors because of their high affinity for CRF receptors. Moreover, the incorporation of radioactive tyrosine creates effective tracers selective for CRFR2 that can be used for high throughout screening purposes.

Lengthening of the peptide chain beyond that which is hereinafter described is expected to provide CRFR2 selective agonists as generally known in this art so long as the cyclic core structure is retained.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser L-serine, Orn=L-ornithine, Nle=L-norleucine, Nva=L-norvaline, Agl=aminoglycine, Abu=L-2-aminobutyric acid, Dbu L-2,4-diaminobutyric acid, Dpr=L-2,3-diaminopropionic acid, Hly=L-homolysine and Har=L-homoarginine. In addition the following abbreviations are used: CML=$C^\alpha CH_3$-L-leucine; Aib=$C^\alpha CH_3$-L-alanine or 2-aminoisobutyric acid; Nal=L-β-(1- or 2-naphthyl) alanine, Pal=L-β-(2-,3- or 4-pyridyl)alanine, Cpa=L-(2-, 3-, or 4-chloro) phenylalanine, Aph=L-(2-,3- or 4-amino) phenylalanine, Amp=(2-, 3- or 4-aminomethyl) phenylalanine, and Nic=3-carboxypyridine (or nicotinic acid).

Generally, one CRF receptor ligand having antagonistic properties will include a D-isomer in the 11-position (which is the N-terminus unless the peptide is extended as by 1, 2 or 3 residues), will preferably include a cyclizing linkage between the residues in the 31-position and the 34-position, and will have the following amino acid sequence or be an equivalent nontoxic salt thereof: Y-$R_8$-$R_9$-$R_{10}$-D-Phe-$R_{12}$-$R_{13}$-$R_{14}$-Arg-$R_{16}$-Nle-$R_{18}$-$R_{19}$-$R_{20}$-$R_{21}$-$R_{22}$-$R_{23}$-$R_{24}$-$R_{25}$-$R_{26}$-$R_{27}$-$R_{28}$-Gln-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$NH_2$ wherein Y is H or an acylating agent having up to 7 carbon atoms or radioiodinated tyrosine; $R_8$ is Asp or des-$R_8$; $R_9$ is Leu or des-$R_9$; $R_{10}$ is Ser, Thr or des-$R_{10}$; $R_{12}$ is His or Glu; $R_{13}$ is CML or Leu; $R_{14}$ is Leu or CML; $R_{16}$ is Glu, CML or Lys; $R_{18}$ is Leu, CML, Ile, Ala or Aib; $R_{19}$ is Glu, D-Glu or His; $R_{20}$ is Ile or Leu; $R_{21}$ is Ala, D-Ala, Aib, Thr, D-Thr, Glu or D-Glu; $R_{22}$ is Arg or Lys; $R_{23}$ is Gln or Ala or Aib; $R_{24}$ is Glu or Asp; $R_{25}$ is Lys or Gln; $R_{26}$ is Glu, Leu or CML; $R_{27}$ is Lys, Ala or Aib; $R_{28}$ is Gln or Glu; $R_{30}$ is Ala or Aib; $R_{31}$ is Glu or Gln; $R_{32}$ is Asn or Ser; $R_{33}$ is Asn or Aib; $R_{34}$ is Lys, Lys(Ac) or Orn; $R_{35}$ is Leu or Ile; $R_{36}$ is CML or Leu; $R_{37}$ is Leu or Nle; $R_{38}$ is Asp or Glu; $R_{39}$ is CML, Ile or Leu; $R_{40}$ is Ile, Ala, Gly, Val, Leu, Nle, Phe, Nva or Gln; wherein D-Phe may be substituted by D-Leu, D-Tyr, D-Cpa, D-Nal or D-Pal or the corresponding L-isomer; provided that a cyclizing bond may exist between $R_{31}$ and $R_{34}$. By lengthening these peptides at the N-terminus, CRFR2 ligands which are agonists may be created.

Another group of ligands which have CRF antagonist properties and bind selectively to CRFR2, have the general formula: Y-$R_9$-$R_{10}$-$R_{11}$-D-Phe-$R_{13}$-$R_{14}$-Leu-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-Glu-$R_{33}$-$R_{34}$-$R_{35}$-$R_{36}$-$R_{37}$-Nle-$R_{39}$-$R_{40}$-$R_{41}$-$NH_2$ wherein Y is an acyl group having up to 15 carbon atoms; $R_9$ is Asp or des-$R_9$; $R_{10}$ is Leu or des-$R_{10}$; $R_{11}$ is Thr or Ser or des-$R_{11}$; $R_{13}$ is His, Tyr or Glu; $R_{14}$ is CML or Leu; $R_{17}$ is Glu, CML, Asn or Lys; $R_{18}$ is Val, Nle, CML or Met; $R_{19}$ is Leu or Ile; $R_{20}$ is Glu, D-Glu, or His; $R_{22}$ is Ala, D-Ala, Aib, Asp, Thr, D-Thr, Glu or D-Glu; $R_{23}$ is Arg or Lys; $R_{24}$ is Ala, Aib or CML; $R_{25}$ is Glu or Asp; $R_{26}$ is Gln, Asn or Lys; $R_{27}$ is Leu or CML; $R_{28}$ is Ala, Lys, Aib or Arg; $R_{29}$ is Gln, Aib or Glu; $R_{30}$ is Gln or Glu; $R_{31}$ is Ala or Aib; $R_{32}$ is Glu or Gln; $R_{33}$ is Ser or Thr; $R_{34}$ is Asn or Aib; $R_{35}$ is Lys or Orn; $R_{36}$ is Lys, Orn, Arg, Har, CML or Leu; $R_{37}$ is Leu, CML, or Tyr; $R_{39}$ is Glu, Aib or Asp; $R_{40}$ is CML, Ile, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln; wherein D-Phe$^{12}$ may be substituted by D-Leu, D-Tyr, D-Cpa, D-Nal or D-Pal, or by the corresponding L-isomer; provided that a cyclizing bond may exist between $R_{32}$ and $R_{35}$.

One more group of ligands which exhibit CRF antagonist and Ucn antagonist properties and bind selectively to CRFR2 have the following amino acid sequence: Y-$R_8$-$R_9$-$R_{10}$-D-Phe-His-$R_{13}$-Leu-Arg-Thr-Leu-Leu-$R_{19}$-Leu-Ala-Arg-Thr-Gln-Ser-Gln-Arg-Glu-Arg-Ala-$R_{31}$-Gln-Asn-$R_{34}$-Ile-$R_{36}$-Phe-$R_{38}$-$R_{39}$-Val-$NH_2$, wherein Y is H or an acylating agent having up to 7 carbon atoms or radioiodinated tyrosine; $R_8$ is Asp or des-$R_8$; $R_9$ is Leu or des-$R_9$; $R_{10}$ is Thr, Ser or des-$R_{10}$; $R_{13}$ is CML or Leu; $R_{19}$ is Glu or Ala; $R_{31}$ is Glu or Gln; $R_{34}$ is Lys or Orn; $R_{36}$ is Ile, C$^\alpha$MeIle or CML; $R_{38}$ is Asp or Ala; $R_{39}$ is CML, Ser or Thr; provided that wherein D-Phe may be substituted by D-Leu, D-Tyr, D-Cpa, D-Nal or D-Pal or by the corresponding L-isomer; and provided further that a cyclizing bond may exist between $R_{31}$ and $R_{34}$.

A preferred group of CRFR2 ligands has the following amino acid sequence (including nontoxic salts thereof): Y-D-Phe-His-CML-Leu-Arg-Lys-Nle-$R_{18}$-$R_{19}$-Ile-Glu-Lys-Gln-$R_{24}$-$R_{25}$-$R_{26}$-$R_{27}$-Gln-Gln-$R_{30}$-Glu-Asn-Asn-$R_{34}$-Leu-Leu-Leu-$R_{38}$-CML-Ile-$NH_2$ wherein Y is Ac or H; $R_{18}$ is CML, Leu, Ile, Ala or Aib; $R_{19}$ is Glu or D-Glu; $R_{24}$ is Asp or Glu; $R_{25}$ is Lys or Gln; $R_{26}$ is Glu, Leu or CML; $R_{27}$ is Lys, Ala or Aib; $R_{30}$ is Ala or Aib; $R_{34}$ is Lys, Lys(Ac) or Orn; and $R_{38}$ is Glu or Asp; and wherein D-Phe may be substituted by D-Leu or D-Tyr, and wherein Glu$^{31}$ maybe joined by a cyclizing bond to $R_{34}$;

Specific analogs of this group which are considered to be particularly biopotent:

cyclo(31–34) [D-Phe$^{11}$, His$^{12}$, Nle$^{17}$, Glu$^{31}$, Lys$^{34}$]Svg (11–40);

cyclo(31–34) [D-Phe$^{11}$, His$^{12}$, CML$^{13}$, Nle$^{17}$, Glu$^{31}$, Orn$^{34}$] Svg (11–40);

cyclo (31–34)[D-Tyr$^{11}$, His$^{12}$, CML$^{13}$, Nle$^{17}$, Glu$^{31}$, Lys$^{34}$] Svg(11–40);

cyclo(31–34) [D-Phe$^{11}$, His$^{12}$, CML$^{13,39}$, Nle$^{17}$, Glu$^{31}$, Lys$^{34}$] Svg(11–40);

cyclo(31–34) [D-Phe$^{11}$, Nle$^{17}$, Glu$^{31}$,Orn$^{34}$] Svg(11–40); and cyclo(31–34) [D-Phe$^{11}$, His$^{12}$, CML$^{13,39}$, Nle$^{17}$, Glu$^{31}$, Lys$^{34}$]Svg(11–40).

The counterparts which are based on Svg (8–40) as well as those which are linear are also included. Moreover, any of the foregoing may be and preferably is acetylated at the n-terminus.

When tyrosine is present at or near the N-terminus, the peptide can be conveniently radiolabelled using $^{125}$I and provides an effective tracer that is CRFR2 selective. By extending the chain length, as generally known in this art, CRFR2 selective agonists may be provided.

The peptides are synthesized by a suitable method, such as by exclusively solid-phase techniques, by partial solid-phase techniques, by fragment condensation or by classical solution addition. Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

The peptides are preferably prepared using solid phase syntheses, such as described by Burgess, K., Solid-Phase Organic Synthesis (John Wiley & Sons 2000), or by Merrifield, *J. Am. Chem. Soc.*, 85, p 2149 (1964). Thus, CRFR2 ligands can be prepared in a straightforward manner and then simply tested for biological activity; this facilitates the ready preparation and evaluation of such peptides. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for a ligand can be prepared, for example, by attaching alpha-amino-protected Ile to an MBHA resin.

After the desired amino acid sequence has been completed, the intermediate peptide is removed from the resin support unless it is desired to form the cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups and the alpha-amino protecting group, if still present, to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The cyclizing step for the CRF peptide analog depends, of course, upon the type of linkage which is desired between the residues in the 31- and 34-positions. To effect an amide cyclizing linkage (lactam bridge), cyclization may be carried out while the partially protected peptide remains attached to the resin as disclosed in U.S. Pat. Nos. 5,064,939 and 5,043,322, the disclosures of which are incorporated herein by reference. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 31-position residue and a side-chain amino group of the 34-position residue, or vice-versa which is considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the N-terminal residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. Following cyclization, the peptide is completely deprotected and cleaved from the resin using a reagent, such as HF. Optionally, a BOC-protecting group can be first removed from the N-terminus using TFA.

Alternatively, cyclizations of peptides by such amide linkages can also be effected using teachings of U.S. Pat. No. 4,115,554, (Sep. 19, 1978); U.S. Pat. No. 4,133,805 (Jan. 9, 1979); U.S. Pat. No. 4,140,767 (Feb. 20, 1979); U.S. Pat. No. 4,161,521 (Jul. 17, 1979); U.S. Pat. No. 4,191,754 (Mar. 4, 1980); U.S. Pat. No. 4,238,481 (Dec. 9, 1980); U.S. Pat. No. 4,244,947 (Jan. 13, 1981); and U.S. Pat. No. 4,261,885 (Apr. 14, 1981).

Set forth hereinafter in the Examples are certain preferred methods for synthesizing these peptides; however, those of skill in the art will readily recognize techniques for synthesizing the invention peptides, see, e.g., Weng and White, Fmoc Solid Phase Peptide Synthesis: A Practical Approach (Oxford Univ Press, 2000); Marshak and Liu, Therapeutic Peptides and Proteins: Formulation, Delivery, and Targeting (Current Communications in Molecular Biology) (Cold Spring Harbor Laboratory 1989); Cabilly, S., Combinatorial Peptide Library Protocols, $1^{st}$ edition (Humana Press, 1998); Crabb, J. W., Techniques in Protein Chemistry V (Academic Press 1994); and Lloyd-Williams et al., Chemical Approaches to the Synthesis of Peptides and Proteins (New Directions in Organic and Biological Chemistry) (CRC Press 1997).

A candidate CRFR2 ligand is also easily evaluated in a binding assay using known CRF receptors, such as that described in Perrin, M., et al., *Endocrinology,* 118, 1171–1179 (1986). CRF receptors and the details of binding assays are discussed later in this specification. Very generally, a binding assay may be carried out with human CRF-R1 using a radioligand such as (cyclo 30–33) [$I^{125}$-D-Tyr$^{12}$, Glu$^{30}$, Lys$^{33}$, Nle$^{21,38}$]-r/hCRF(12–41) or its analog having D-His$^{32}$, which have high affinity for the human CRF-R1. For example, the first-named compound has a $K_D$ of 2.0 nanomolar (1.4–2.9) for binding to hCRFR1, which is essentially equal to that of the comparable D-Phe$^{12}$ analog. One such representative binding assay utilizing CRF-R1 receptor is described in Chen, et al., *P.N.A.S.,* 90, 8967–8971 (October 1993). Such assays are advantageously used to screen for potential CRF-like ligands, in peptide or other form, using a labelled cyclic CRF analog, preferably such a labelled cyclic CRFR2 ligand with high affinity.

CRF receptors have now been cloned and are disclosed in the aforementioned Chen et al. article, in Perrin, M., et al., *P.N.A.S,* 92, 2969–2973 (March 1995), and in Lovenberg, T., et al., *P.N.A.S.,* 92, 836–840 (January 1995). Binding affinity is a term used to refer to the strength of interaction between ligand and receptor. To demonstrate binding affinity for a CRF receptor, the peptides of the invention are easily evaluated using a tracer ligand of known affinity, such as $^{125}$I-radiolabelled oCRF or [D-Tyr$^{12}$, Nle$^{21,38}$]-r/hCRF (12–41), in binding assay experiments which are well known in this art. The results of such assays indicate the affinity at which each ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. However, so long as these assays are carefully performed under specific conditions with relatively low concentrations of receptor or the like, the calculated $K_i$ will be substantially the same as its dissociation constant $K_D$. Dissociation constant $K_D$ is representative of the concentration of ligand necessary to occupy one-half (50%) of the binding sites of a receptor or the like. It is particularly efficient to test for $K_i$ because only a single tracer need be labelled, e.g. radioiodinated. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number. Alternatively, competitive assays can generate $IC_{50}$ values which are indicative of the concentration of a competitive ligand necessary to displace a saturation concentration of a target ligand being measured from 50% of binding sites. Those reported hereinafter are derived using radioactively labeled [Tyr Glu$^1$, Nle$^{17}$]-Svg as a radioligand.

With respect to a particular receptor protein, a CRF analog peptide having a $K_D$ or an $IC_{50}$ of about 10 nM or less means that a concentration of the ligand (i.e., the CRF analog peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10–20 pmol receptor/mg membrane protein). Preferred peptides provided by this invention have a binding affinity ($K_D$ or $IC_{50}$) such that a ligand concentration of about 10 nanomolar or less is required in order to occupy (or bind to) at least 50% of the receptor binding sites, and these are considered to have high affinity. Some of these CRF analog peptides have a binding affinity of about 2 nM or less. Generally, for purposes of this application, a dissociation constant of about 5 nanomolar or lower is considered to be an indication of strong affinity, and a binding affinity of about 2 nanomolar or less is an indication of very strong affinity. As mentioned above, it is considered to be particularly advantageous that these CRF analog peptides have a substantially higher affinity for the family of CRFR2 receptors so that they are thus selective in their biological effect.

These binding assays employing CRF receptors are straightforward to perform and can be readily carried out with initially identified or synthesized peptides to determine whether such peptides will likely be effective and selective CRFR2 ligands. Such binding assays can be carried out in a variety of ways as well known to one of skill in the art. One detailed example of such an assay is set forth in the Perrin, M., et al., *Endocrinology* article, and another is described in DeSouza et al., *J. Neuroscience*, 7:88 (1987).

In addition to inhibiting CRF receptor binding, a candidate's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The inhibition of CRF-stimulated adenylate cyclase activity, determined by the assay described by G. Battaglia et al., *Synapse* 1:572 (1987), provides an assay for determining a compound's ability to antagonize CRF activity. Accordingly, CRF receptor antagonist activity may be determined by assay techniques which generally include an initial binding assay followed by such a cAMP screening protocol.

The following Example 1 sets forth a preferred method for synthesizing CRFR2 ligands of interest by a solid-phase technique. These examples are offered by way of illustration and not limitation.

EXAMPLE 1

The synthesis of the (cyclo 31–34)[Ac-D-Phe[11], His[12], CML [13,39], Nle[17], Glu[31], Lys[34]]-sauvagine(11–40) having the amino acid sequence: Ac-D-Phe-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$ is conducted in a stepwise manner on about 3 grams of a MBHA hydrochloride resin, such as available from Bachem, Inc., having a substitution range of about 0.1 to 0.5 mmoles/gm. resin. The synthesis is performed manually on an MBHA resin that has a substitution of about 0.28 mequiv per gram of resin using a protocol such as that which follows:

| STEP | REAGENTS AND OPERATIONS | MIX TIMES MIN. |
|---|---|---|
| 1 | Methanol (MeOH) wash | 1 |
| 2 | 10% TEA/DCM (v/v) wash | 1 |
| 3 | Methanol (MeOH) wash | 1 |
| 4 | DCM wash (3 times) | 3 |
| 5 | 80 percent TFA plus 5 percent m-cresol in CH$_2$Cl$_2$ | 10 |
| 6 | Methanol (MeOH) wash | 1 |
| 7 | TEA 10% in DCM | 1 |
| 8 | MeOH wash | 1 |
| 9 | TEA 10% in DCM | 1 |
| 10 | DCM wash (3 times) | 3 |
| 11 | BOC-amino acid (4 equiv. in 30 ml. of either DCM or NMP depending upon the solubility of the particular protected amino acid, (1 time) plus DIC (4 equiv) in CH$_2$Cl$_2$ | 20–30 |

After deprotection and neutralization, the peptide chain is built step-by-step on the resin. Generally, one to two mmol. of BOC-protected amino acid in methylene chloride is used per gram of resin (e.g. a 2–5 fold excess depending on substitution of the resin), plus one equivalent of 2 molar DIC in methylene chloride (DCM), for two hours. When BOC-Arg(Tos) is being coupled, a mixture of 50% NMP and methylene chloride is used. Bzl is used as the hydroxyl side-chain protecting group for Ser. BOC-Asn(Xan) or BOC-Gln(Xan) is coupled in the presence of one equivalent of DIC and two equivalents of HOBt in a 50% mixture of DMF and methylene chloride. Either 2Cl-Z or Fmoc is used as the protecting group for the Lys side chain depending upon whether it is to be part of a lactam bridge. Tos is used to protect the guanidino group of Arg and the imidazole group of His, and the side chain carboxyl group of Glu is protected by OChx or OFm depending upon whether it is to take part in the cyclizing reaction. At the end of the synthesis, the following composition is obtained: BOC-D-Phe-His(Tos)-CML-Leu-Arg(Tos)-Lys(2Cl-Z)-Nle-Ile-Glu(OChx)-Ile-Glu(OChx)-Lys(2Cl-Z)-Gln(Xan)-Glu(OChx)-Lys(2ClZ)-Glu(OChx)-Lys(2CLZ)-Gln(Xan)-Gln(Xan)-Ala-Glu(OFm)-Asn(Xan)-Asn(Xan)-Lys(Fmoc)-Leu-Leu-Leu-Asp(OChx)-CML-Ile-MBHA resin support.

The peptide-resin is then treated with TFA to remove the BOC protecting group at the N-terminus. After neutralization, it is reacted with acetic anhydride to acetylate the aspartic acid residue.

Next cyclization (lactamization) of residues 31 and 34 is performed by the method referred to hereinbefore and described more fully as follows. After washes with dichloromethane(DCM) (2×) and N-methylpyrrolidone (NMP) (2×), the OFmc/Fmoc groups of Glu[31] and Lys[34], respectively, are removed by 20% piperidine in NMP (1×1 min. and 2×10 min.), followed by washing with NMP (2×), Et$_3$N in CH$_2$Cl$_2$(1×) methanol (MeOH) (2×) and DCM (2×). The peptide-resin is cyclized by reaction at room temperature with twofold excess of HBTU or O-(benzotriazol-1-yl)-1,1,3,3-tetramethyluronium borate (TBTU) in presence of excess diisoproplyethylamine (DIEA) in NMP for 30 minutes. Other suitable reagents are well known in the art and may alternatively be used. After washing, the cyclization may be repeated if desired to assure completion. The reaction is followed by Kaiser ninhydrin test (E. Kaiser et al., "Color test for detection of free terminal amino groups in the solid-phase synthesis of peptides", *Anal Biochem* (1970) 34:595–98).

About 2 grams of the resin-peptide is cleaved by anhydrous HF (20 mL) in the presence of p-cresol (2 g) at 0° C. for 90 min. The crude peptide is precipitated and washed with anhydrous diethyl ether (450 mL in 3 portions), filtered, extracted from the resin with 200 mL (4 portions) of 0.1% TFA in $CH_3CN/H_2O$ (60:40) and lyophilized to give the crude product.

The crude lyophilized peptide is purified by preparative reverse-phase HPLC (RP-RHPLC) on a system composed of a Waters Associates (Milford, Mass.) Prep LC 3000 System, a Waters Associate 600E System Controller, a Shimadzu SPD-6A UV Spectrophotometric variable-wavelength detector (detection was 220 nm), Waters 1000 PrepPak Module, and a Fisher (Lexington, Mass.) Recordall Series 5000 strip chart recorder (chart speed 0.5 cm/min.). The peptide purification is carried out in three steps using buffers of TEAP pH 2.25, TEAP pH 6.8 and 0.1% TFA.

The crude peptide (about 0.3–1.5 gm) is first dissolved in 100 mL buffer B: triethylammonium phosphate (TEAP) (pH 2.25) filtered on 0.45 μm pore size nylon filter disc, then diluted with 150 ml deionized water, and loaded on a preparative reversed phase HPLC cartridge (5×30 cm) packed in the laboratory using Waters polyethylene sleeves and frits and Vydac $C_{18}$ silica gel (The Separations Group, Hesperia, Calif.; 300 Å pore size, 15 to 20-μm particle size). The peptide is eluted using buffer B: 60% $CH_3CN$ in buffer A with a gradient from 40 to 100% B over 120 minutes at a change rate of about 0.5% per min. Buffers A (triethlyammonium phosphate (TEAP), pH 2.25) and B ($CH_3CN$ in A) are pumped at a flow rate of 100 mL/min until the major component elutes. The column is washed with 100% Buffer B to eliminate all contamination. Fractions containing a total of 50–100 mL are screened under isocratic conditions (68% B), and fractions containing the compound are identified and pooled.

In the second step, the pooled fractions are diluted with the same amount of $H_2O$, the pH adjusted to 6.8 with triethylamine and loaded onto the column. The peptide is eluted using buffer A: TEAP, pH 6.8 and buffer B: 60% $CH_3CN$ in buffer A. A gradient from 40 to 100% B in 60 minutes was used, at 1%/min, with the same flow rates. Fractions containing a total of 30–50 mL are screened, and fractions containing the compound are pooled.

In the third step, the pooled fractions of the second step purification are diluted with the same amount of demonized water, acidified with 1 mL of TFA and loaded to the column. Elution is carried out using buffer A: 0.1% TFA in water and buffer B: 60% acetonitrile in buffer A, at a gradient of 40–100%/30 minutes (2%/min). Fractions containing a total of 30–50 mL are screened, and fractions containing the compound are pooled and lyophilized to yield the final product peptide.

The synthesis is repeated omitting the cyclization step (i.e. by substituting Gln in the 31-position and acetylating the side-chain of Lys in the 34-position to produce a comparable linear peptide.

Purity of about 96% or higher for the peptides is confirmed by HPLC and by capillary zone electrophoresis (CZE), and identity is confirmed by mass spectroscopy (MS). The measured value of 3725.1 obtained using liquid secondary ion mass spectrometry (LSIMS) for the cyclic peptide is in agreement with the calculated value of 3725.14. The linear peptide has a measured value of 3784.00 which corresponds to the calculated value of 3784.18.

Binding assays with cells expressing human CRFR1 are carried out as described in the Chen et al. *P.N.A.S.*, supra. The affinities of test peptides for CRFR1 and CRFR2b stably expressed in CHO cells were determined by competitive displacement of $^{125}$I-(Nle$^{21}$, Tyr$^{32}$) ovine CRF (for CRFR1) or of [$^{125}$I-Tyr$^o$-]Ucn (for CRFR2b) as described. Data from at least 3 experiments were pooled and inhibitory dissociation constant ($K_i$) values (95% confidence limits) were calculated using the LIGAND program of Munson and Rodbard (1980), *Anal. Biochem*, 107:220–239. The cloned hCRFR1 binds the cyclic peptide with only low affinity as determined by the competitive displacement of bound radioligand. The $K_i$ was determined to be about 1000 nM, which may be compared to sauvagine (Svg) which binds very strongly, i.e. about 0.94 nM. The linear peptide exhibits a $K_i$ of 460 nmol. The difference is dramatic for similar stably transfected CHO cells expressing human CRFR2b where the respective results for the cyclic and linear peptides were 1.1 nM and 1.9 nM, indicating strong binding, comparable to Svg which has a $K_i$ of about 1.73 nM for CRFR2b. Assaying with cells expressing CRFR1, the $IC_{50}$'s are greater than 500 nM and greater than 100 nM respectively, for the cyclic and linear peptides. The $IC_{50}$'s are greater than 500 nM and greater than 100 nM, Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 2

The synthesis of Example 1 is repeated, extending the N-terminus by 3 residues, to produce the following peptide:

(cyclo 31–34)[Ac-D-Phe$^{11}$, His$^{12}$, CML$^{13,39}$, Nle$^{17}$, Glu$^{31}$, Lys$^{34}$]-sauvagine(8–40) having the amino acid sequence: Ac-Asp-Leu-Ser-D-Phe-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The synthesis is repeated once omitting the cyclization step (i.e. by protecting all Glu residues with OChx and all Lys residues with 2Cl-Z) to produce a comparable linear peptide.

Each peptide has a purity of about 95% or higher as a result of HPLC, which is confirmed by CZE. The measured values of 4040.2 and 4058.0 obtained using LSIMS for the cyclic and linear peptides respectively, are in agreement with the calculated values of 4040.28 and 4058.30. The cloned hCRFR1 binds the cyclic peptide with only low affinity as determined by the competitive displacement of bound radioligand. The $K_i$ was determined to be about 543 nM, which may be compared to sauvagine (Svg) which binds very strongly, i.e. about 0.94 nM. The linear peptide exhibits a $K_i$ of 128 nmol. The difference is dramatic for similar stably transfected CHO cells expressing human CRFR2b where the respective results for the cyclic and linear peptides were $IC_{50}$'s of 1.3 nM and 0.92 nM, indicating strong binding, comparable to Svg which has a $K_i$ of about 1.73 nM for CRFR2b. Assaying with cells expressing CRFR1, the $IC_{50}$'s were greater than 500 nM for the cyclic peptide and greater than 100 nM for the linear peptide. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 2A

The synthesis of Example 1 is repeated, again extending the N-terminus by 3 residues, but this time, instead of cyclizing the peptide, comparable residues are used in the 31- and 34-positions which have amides in their side chains to produce the following peptide: [Ac-D-Phe$^{11}$, His$^{12}$ CML$^{13,39}$, Nle$^{17}$, Gln$^{31}$, Lys(Ac)$^{34}$]-sauvagine(8–40) having the amino acid sequence: Ac-Asp-Leu-Ser-D-Phe-His-CML-Leu-Arg-Lys-Nle-Ile-Glu-Ile-Glu-Lys-Gln-Glu-Lys-Glu-Lys-Gln-Gln-Ala-Gln-Asn-Asn-Lys(Ac)-Leu-Leu-Leu-Asp-CML-Ile-NH$_2$.

It has a purity of greater than 98% as a result of HPLC, which is confirmed by CZE. The measured value of 4099.2 obtained using LSIMS is in agreement with the calculated value of 4099.32. The cloned hCRFR1 binds the cyclic peptide with only low affinity, i.e. greater than 100 nM, as determined by the competitive displacement of bound radioligand. For similar, stably transfected CHO cells expressing human CRFR2b, the IC$_{50}$ for the modified linear peptide was 0.60 nM, indicating strong binding.

EXAMPLE 3

The synthesis of Example 1 is repeated, substituting D-Leu for D-Phe at the N-terminus, to produce the following peptide:

(cyclo 31–34)[Ac-D-Leu$^{11}$, His$^{12}$, CML$^{13,39}$, Nle$^{17}$, Glu$^{31}$ Lys$^{34}$]-sauvagine(8–40) having the amino acid sequence: Ac-Asp-Leu-Ser-D-Leu-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 4

The synthesis of Example 1 is repeated, substituting D-Tyr for D-Phe at the N-terminus, to produce the following peptide:

(cyclo 31–34)[Ac-D-Tyr$^{11}$, His$^{12}$, CML$^{13,39}$, Nle$^{17}$, Glu$^{31}$, Lys$^{34}$]-sauvagine(11–40) having the amino acid sequence: Ac-D-Tyr-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 5

The synthesis of Example 1 is repeated, substituting D-Cpa for D-Phe at the N-terminus, to produce the following peptide:

(cyclo 31–34)[Ac-D-Cpa$^{11}$, His$^{12}$, CML$^{13,39}$, Nle$^{17}$, Glu$^{31}$, Lys$^{34}$]-sauvagine(11–40) having the amino acid sequence: Ac-D-Cpa-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 6

The synthesis of Example 1 is repeated, substituting D-2Nal for D-Phe at the N-terminus, to produce the following peptide:

(cyclo 31–34)[Ac-D-2Nal$^{11}$, His$^{12}$, CML$^{13,39}$, Nle$^{17}$, Glu$^{31}$, Lys$^{34}$]-sauvagine(11–40) having the amino acid sequence: Ac-D-2Nal-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 7

The synthesis of Example 1 is repeated, substituting D-3Pal for D-Phe at the N-terminus, to produce the following peptide:

(cyclo 31–34)[Ac-D-3 Pal$^{11}$, His$^{12}$, CML$^{13,39}$, Nle$^{17}$, Glu$^{31}$, Lys$^{34}$]-sauvagine(11–40) having the amino acid sequence: Ac-D-3 Pal-His-CML-Leu-Arg-Lys-Nle-Ile-Glu-Ile-Glu-Lys-Gln-Glu-Lys-Glu-Lys-Gln-Gln-Ala-Glu-Asn-Asn-Lys-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 8

The synthesis of Example 1 is repeated, substituting Orn for Lys in the 34-position, to produce the following peptide:

(cyclo 31–34)[Ac-D-Phe$^{11}$, His$^{12}$, CML$^{13,39}$, Nle$^{17}$, Glu$^{31}$, Orn$^{34}$]-sauvagine(11–40) having the amino acid sequence: Ac-D-Phe-His-CML-Leu-Arg-Lys-Nle-Ile-Glu-Ile-Glu-Lys-Gln-Glu-Lys-Glu-Lys-Gln-Gln-Ala-Glu-Asn-Asn-Orn-Leu-Leu-Leu-Asp-CML-Ile-NH$_2$.

The peptide binds significantly more strongly to CRFR2 than to CRFR1 showing very good selectivity. Standard assaying for a cAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 9

A synthesis similar to that of Example 1 is carried out to produce the following peptide:

(cyclo 32–35) [D-Phe$^{12}$, Nle$^{21,38}$, Glu$^{32}$, Lys$^{35}$]-r/hCRF (12–41), having the formula:

(cyclo 32–35)D-Phe-His-Leu-Leu-Arg-Glu-Val-Leu-Glu-Nle-Ala-Arg-Ala-Glu-Gln-Leu-Ala-Gln-Gln-Ala-Glu-Ser-Asn-Lys-Lys-Leu-Nle-Glu-Ile-Ile-NH$_2$.

It has a purity of about 97% which is confirmed by CZE. A measured value of 3483.9 is obtained using LSIMS and is in agreement with the calculated value of 3483.98. The cloned hCRFR1 binds the cyclic peptide with only low affinity, i.e. greater than 100 nM, as determined by the competitive displacement of bound radioligand. For similar, stably transfected CHO cells expressing human CRFR2b, the IC$_{50}$ for the cyclic peptide was 10 nM, indicating substantially stronger binding.

EXAMPLE 9A

A synthesis similar to that of Example 1 is carried out to produce the following peptide:

(cyclo 32–35) [Ac-Asp$^9$-D-Phe$^{12}$, Nle$^{21,38}$, Glu$^{32}$, Lys$^{35}$]-r/hCRF(9–41), having the formula:

(cyclo 32–35) [Ac-Asp$^9$-D-Phe$^{12}$, Nle$^{21,38}$, Glu$^{32}$, Lys$^{35}$]-r/hCRF(9–41), having the formula:

(cyclo 32–35)Ac-Asp-Leu-Thr-D-Phe-His-Leu-Leu-Arg-Glu-Val-Leu-Glu-Nle-Ala-Arg-Ala-Glu-Gln-Leu-Ala-Gln-Gln-Ala-Glu-Ser-Asn-Lys-Lys-Leu-Nle-Glu-Ile-Ile-NH$_2$.

The cloned hCRFR1 binds the cyclic peptide with only low affinity, i.e. greater than 100 nM, as determined by the competitive displacement of bound radioligand. For similar, stably transfected CHO cells expressing human CRFR2b, the cyclic peptide shows substantially stronger binding.

EXAMPLE 9B

A synthesis similar to that of Example 9 is carried out substituting CML for Leu$^{14}$ and for Ile$^{40}$ to produce the following peptide:

(cyclo 32–35) [D-Phe$^{12}$, CML$^{14,40}$, Nle$^{21,38}$, Glu$^{32}$, Lys$^{35}$]-r/hCRF(12–41), having the formula:

(cyclo 32–35)D-Phe-His-CML-Leu-Arg-Glu-Val-Leu-Glu-Nle-Ala-Arg-Ala-Glu-Gln-Leu-Ala-Gln-Gln-Ala-Glu-Ser-Asn-Lys-Lys-Leu-Nle-Glu-CML-Ile-NH$_2$.

The cloned hCRFR1 binds the cyclic peptide with only low affinity, i.e. greater than 100 nM. For similar, stably transfected CHO cells expressing human CRFR2b, the cyclic peptide shows substantially stronger binding.

EXAMPLE 9C

A synthesis similar to that of Example 9A is carried out to produce the following linear peptide: D-Phe-His-Leu-Leu-Arg-Glu-Val-Leu-Glu-Nle-Ala-Arg-Ala-Glu-Gln-Leu-Ala-Gln-Gln-Ala-Glu-Ser-Asn-Lys(Ac)-Lys-Leu-Nle-Glu-Ile-Ile-NH$_2$.

The cloned hCRFR1 binds the cyclic peptide with only low affinity, i.e. greater than 100 nM. For similar, stably transfected CHO cells expressing human CRFR2b, the linear peptide shows substantially stronger binding.

EXAMPLE 10

The peptide (cyclo 31–34) [D-Tyr$^{11}$, Lys$^{34}$], -Ucn(11–40), having the amino acid sequence: H-D-Tyr-His-Leu-Leu-Arg-Thr-Leu-Leu-Glu-Leu-Ala-Arg-Thr-Gln-Ser-Gln-Arg-Glu-Arg-Ala-Glu-Gln-Asn-Lys-Ile-Ile-Phe-Asp-Ser-Val-NH$_2$ is synthesized in the manner described in Example 1, with the cyclizing lactam bond being created as described in Example 1 of U.S. Pat. No. 5,064,939.

The peptide binds significantly more strongly to CRFR2 than to CRFR1 showing very good selectivity. Standard assaying for a CAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

When iodinated, the $^{125}$I-D-Tyr$^{11}$ cyclic analog is useful in screening assays and the like.

EXAMPLE 10A

The peptide (cyclo 31–34)[D-Phe$^{11}$, Lys$^{34}$]-Ucn(11–40), having the amino acid sequence: H-D-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Lys-Ile-Ile-Phe-Asp-Ser-Val-NH$_2$ is synthesized in the manner described in Example 1, with the cyclizing lactam bond being created as described in Example 1 of U.S. Pat. No. 5,064,939.

The peptide binds significantly more strongly to CRFR2 than to CRFR1 showing very good selectivity. Standard assaying for a CAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

The above synthesis is repeated twice to substitute D-Leu and D-Pal for D-Phe. The peptides show similar selectivity as Ucn antagonists.

EXAMPLE 10B

The peptide [D-Phe$^{11}$, Gln$^{31}$,Lys(Ac)$^{34}$]-Ucn(11–40), having the amino acid sequence: H-D-Phe-His-Leu-Leu-Arg-Thr-Leu-Leu-Glu-Leu-Ala-Arg-Thr-Gln-Ser-Gln-Arg-Glu-Arg-Ala-Gln-Gln-Asn-Lys(Ac)-Ile-Ile-Phe-Asp-Ser-Val-NH$_2$ is synthesized in the manner described in Example 1.

The peptide binds significantly more strongly to CRFR2 than to CRFR1 showing very good selectivity. Standard assaying for a CAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 10C

The peptide (cyclo 31–34) [Ac-Asp$^8$,D-Phe$^{11}$,Lys$^{34}$]-Ucn (8–40), having the amino acid sequence: Ac-Asp-Leu-Thr-D-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Lys-Ile-Ile-Phe-Asp-Ser-Val-NH$_2$ is synthesized in the manner described in Example 1, with the cyclizing lactam bond being created as described in Example 1 of U.S. Pat. No. 5,064,939.

This synthesis and testing shows that the inclusion of 3 additional L-isomers at the N-terminus along with acylation does not significantly alter its selectivity as a Ucn antagonist.

The peptide binds significantly more strongly to CRFR2 than to CRFR1 showing very good selectivity. Standard assaying for a CAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

EXAMPLE 10D

The peptide [Ac-Asp$^8$,D-Phe$^{11}$,CML$^{13,39}$, Lys$^{34}$]-Ucn (8–40), having the amino acid sequence: Ac-Asp-Leu-Thr-D-Phe-His-CML-Leu-Arg-Thr-Leu-Leu-Glu-Leu-Ala-Arg-Thr-Gln-Ser-Gln-Arg-Glu-Gln-Ala-Glu-Gln-Asn-Lys-Ile-Ile-Phe-Asp-CML-Val-NH$_2$ is synthesized in the manner described in Example 1.

The peptide binds significantly more strongly to CRFR2 than to CRFR1 showing very good selectivity. Standard assaying for a CAMP accumulation in CHO cells stably transfected either with CRFR1 or CRFR2, which cells are being treated with CRF, demonstrates that the peptide is able to effectively antagonize CRF activity with respect to CRFR2 while having little or no effect with respect to CRFR1.

Preferably the cyclic CRF antagonist does not inherently activate CRF receptors. For example, Peptide 1 of Example 1 has only minor intrinsic CRF activity when administered at the highest dosage. Generally a peptide is considered not to significantly activate the CRF receptor when its intrinsic activity measures about 20% or less of the native compound. Preferred antagonists have an intrinsic activity of about 15% or less; however, intrinsic activity is simply one factor to be balanced with its potency as an antagonist.

The compounds and pharmacutical compositions of this invention are useful in the prophylaxis and/or treatment (comprising administering to a mammal, such as a human, an effective amount of such compound, a pharmaceutically acceptable salt thereof, or composition) of (1) diseases and disorders which can be effected or facilitated by modulating CRF, such as by antagonizing CRF, including but not or is radioiodinated tyrosine limited to disorders induced or facilitated by CRF; and (2) inflammatory disorders, such as rheumatoid arthritis and osteoarthritis, pain, asthma, psoriasis and allergies; generalized anxiety disorder such as stress or shock; panic; phobias; obsessive-compulsive disorder; stress disorders such as post-traumatic stress disorder, sleep disorders induced by stress; pain perception such as fibromyalgia; mood disorders such as depression, including major depression, single episode depression, recurrent depression, child abuse induced depression, mood disorders associated with premenstrual syndrome, abnormal aggression, and postpartum depression; dysthemia; bipolar disorders; cyclothymia; chronic fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease; spastic colon, diarrhea and post operative ilius and colonic hypersensitivity associated by psychopathological disturbances or stress, stress-induced fever; eating or feeding disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head and spinal cord trauma; ischemic neuronal damage (e.g., cerebral ischemia such as cerebral hippocampal ischemia); excitotoxic neuronal damage; cardiovascular and heart related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in animals, sheering stress in sheep or human-animal interaction related stress in dogs); urinary incontinence; senile dementia of the Alzheimer's type; multiinfarct dementia; amyotrophic lateral sclerosis; chemical dependencies, withdrawals and addictions (e.a., dependencies on alcohol, cocaine, heroin, benzodiazepines, or other drugs); osteoporosis; psychosocial dwarfism and hypoglycemia in mammals, including humans.

CRFR2 ligands or the nontoxic addition salts thereof, combined with a pharmaceutically acceptable carrier and/or diluent to form a pharmaceutical composition, may be administered to mammals, including humans, either intravenously, subcutaneously, intramuscularly, percutaneously, e.g. intranasally, intracerebroventricularly or orally. As used herein, the terms "pharmaceutically acceptable", "physiologically tolerable" and grammatical variations thereof, as they refer to compositions, carriers, diluents and reagents, are used interchangeably. Preferably, the materials are capable of administration to a mammal without the production of undesirable physiological effects, such as nausea, dizziness, gastric upset and the like. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous glucocorticoid production or for possible uses outlined above. Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRFR2 ligand, diluents, dispersing and surface active agents, binders, and lubricants. One skilled in this art may further formulate the CRF receptor ligand in an appropriate manner, and in accordance with accepted practices, such as those disclosed in Remington's Pharmaceutical Sciences, Gennaro, Ed., Mack Publishing Co., Easton, USA, 1990.

The required dosage will vary with the particular condition being treated, with the severity of the condition and with the duration of desired treatment, and multiple dosages may be used for a single day. In order to block the stress-related effects of endogenous CRF within the central nervous system, it may be necessary to deliver the CRF analogs into the cerebral ventricle or spinal fluid. Alternatively, a means of modifying the analogs so that they could penetrate the blood-brain barrier should be found. For parental administration, solutions in peanut oil, in aqueous propylene glycol, or in sterile aqueous solution may be employed. Such aqueous solutions, which are suitably buffered, are especially suitable for intravenous, intramuscular, subcutaneous and intraperitoneal administration. Sterile aqueous media are readily available.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, hydriodide, cinnamate, sulphate, sulfamate, sulfonate, phosphate, tannate, oxalate, fumarate, gluconate, alginate, maleate, acetate, citrate, benzoate, succinate, malate, ascorbate, tartrate and the like which can be prepared in a conventional manner. If the active ingredient is to be administered in tablet form, the tablet may contain a binder or excipient, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician in single or multiple doses, and pharmaceutical compositions will usually contain the peptide in conjunction with a known, pharmaceutically-acceptable carrier that may extend its duration of action. The effective daily dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal. For the increase of intestinal motility about 0.1 to about 100 mg/kg is generally employed; for treatment of migraines, a dosage of about 0.1 to about 50 mg/kg, may be employed. The daily dosage may be given in a single dose or up to three divided doses.

The use of competitive binding assays is considered particularly valuable for screening candidates for new drugs, e.g. to identify new CRF-like peptides or other compounds having even greater or more selective binding affinity for CRF receptors, which candidates would therefore be potentially useful as drugs. In the assay, one determines the ability of the candidate antagonist to displace the labelled peptide. Such screening assays as described hereinbefore may be used with a radiolabelled cyclic CRF antagonist, to screen for potential CRF agonists. Assays employing a labelled CRF antagonist with high affinity may be used to screen for more potent antagonists of CRF. In such assays, an appropriate cyclic CRF antagonist is appropriately labeled with a substance that is readily detected, such as a radioactive isotope, e.g. $^{125}$I, or an enzyme or some other suitable tag.

As used herein all temperatures are ° C. and all ratios are by volume. Percentages of liquid materials are also by volume. By lower alkyl is meant $C_1$ to $C_6$. The disclosures of all U.S. patents mentioned hereinbefore are expressly incorporated by reference.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, pharmaceutically acceptable salts and other comparable formulations, although not specifically recited, are clearly equivalents of the claimed subject matter. Moreover, substitutions and modifications at various positions throughout the peptide chains as indicated in the first general formulas in the detailed description may be made without detracting from the potency of the analogs. Developments in the field have shown that peptides having the various specified residues at positions 14, 16, 18–30, 32, 33, 35, 36, 38 and 40 in the molecule exhibit CRF activity. As a result, it is well-accepted in this art that a CRF analog having a particular amino acid sequence which exhibits improved biopotency as a result of substitutions elsewhere in the sequence (such as a cyclic peptide having the 31–34 lactam bond described herein for Svg and Ucn or the 32–35 lactam bond for CRF) will retain its improved biopotency even if a number of equivalent substitutions are incorporated in other locations in the molecule. By equivalent is meant a functionally similar pentapeptide, where one or more residues have been substituted by making a conservative substitution, as described in detail in U.S. Pat. No. 6,214,797. The N-terminus of Svg (11–40) can be extended by Thr or Ser, by Leu-Thr or Leu-Ser, or by Asp-Leu-Thr or Asp-Leu-Ser or by other equivalent single residues or di- or tripeptides and/or can be acylated by an acyl group having 12 or less carbon atoms, preferably having 7 or less, e.g. acetyl, and such changes are considered to produce equivalent CRF antagonists. Although, the 11–40 analogs may be preferred because N-terminally extended analogs may exhibit some intrinsic agonist properties, the longer ligands may exhibit longer duration of action. Instead of the simple amide at the C-terminus, a lower alkyl-substituted amide, i.e., 1–4 carbon atoms, e.g., methylamide or ethylamide, may be incorporated. The amino group which is reacted to form the 31–34 lactam cyclizing bond or the α-amino group of one of the residues in positions 31 through 34 may be alkylated, as by adding a methyl group; such changes are considered to create equivalent cyclic peptides which are CRFR2 ligands. All such aforementioned peptides are considered as being within the scope of the invention.

Urocortin is disclosed in U.S. Pat. No. 6,214,797, issued Apr. 10, 2001.

Various features of the invention are emphasized in the claims which follow.

The invention claimed is:

1. A CRFR2 ligand, or a pharmaceutically acceptable salt thereof, which ligand exhibits CRF antagonistic properties and binds selectively to CRFR2 and which has the amino acid sequence:

Y-$R_8$-$R_9$-$R_{10}$-$R_{11}$-$R_{12}$-$R_{13}$-$R_{14}$-Arg-$R_{16}$-Nle-$R_{18}$-$R_{19}$-$R_{20}$-$R_{21}$-$R_{22}$-$R_{23}$-$R_{24}$-$R_{25}$-$R_{26}$-$R_{27}$-$R_{28}$-Gln-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$NH_2$ wherein Y is H or an acyl group having up to 7 carbon atoms or radioiodinated tyrosine; $R_8$ is Asp or des-$R_8$; $R_9$ is Leu or des-$R_9$; $R_{10}$ is Ser, Thr or des-$R_{10}$; $R_{11}$ is D-Phe, D-Leu, D-Tyr, D-Cpa, D-Nal, D-Pal, Phe, Leu, Tyr, Cpa, Nal or Pal; $R_{12}$ is His or Glu; $R_{13}$ is CML or Leu; $R_{14}$ is Leu or CML; $R_{16}$ is Glu, CML or Lys; $R_{18}$ is Leu, CML, Ile, Ala or Aib; $R_{19}$ is Glu, D-Glu or His; $R_{20}$ is Ile or Leu; $R_{21}$ is Ala, D-Ala, Aib, Thr, D-Thr, Glu or D-Glu; $R_{22}$ is Arg or Lys; $R_{23}$ is Gln or Ala or Aib; $R_{24}$ is Glu or Asp; $R_{25}$ is Lys or Gln; $R_{26}$ is Glu, Leu or CML; $R_{27}$ is Lys, Ala or Aib; $R_{28}$ is Gln or Glu; $R_{30}$ is Ala or Aib; $R_{31}$ is Glu or Gln; $R_{32}$ is Asn or Ser; $R_{33}$ is Asn or Aib; $R_{34}$ is Lys, Lys(Ac) or Orn; $R_{35}$ is Leu or Ile; $R_{36}$ is CML or Leu; $R_{37}$ is Leu or Nle; $R_{38}$ is Asp or Glu; $R_{39}$ is CML, Ile or Leu; and $R_{40}$ is Ile, Ala, Gly, Val, Leu, Nle, Phe, Nva or Gln;

wherein a cyclizing bond may exist between the side chains of $R_{31}$ and $R_{34}$ so as to form a cyclo(31–34) structure.

2. The ligand according to claim 1 wherein $R_{31}$ is Gln and $R_{34}$ is Lys(Ac).

3. The CRFR2 ligand according to claim 1 having the amino acid sequence: cyclo(31–34)Y-$R_{11}$-His-CML-Leu-Arg-Lys-Nle-$R_{18}$-$R_{19}$-Ile-Glu-Lys-Gln-$R_{24}$-$R_{25}$-$R_{26}$-$R_{27}$-Gln-Gln-$R_{30}$-Glu-Asn-Asn-$R_{34}$-Leu-Leu-Leu-$R_{38}$-CML-Ile-NH$_2$ wherein Y is Ac or H; $R_{11}$ is D-Phe or D-Leu; $R_{18}$ is CML, Leu, Ile, Ala or Aib; $R_{19}$ is Glu or D-Glu; $R_{24}$ is Asp or Glu; $R_{25}$ is Lys or Gln; $R_{26}$ is Glu, Leu or CML; $R_{27}$ is Lys, Ala or Aib; $R_{30}$ is Ala or Aib; $R_{34}$ is Lys or Orn; and $R_{38}$ is Glu or Asp.

4. The ligand according to claim 3 wherein $R_{24}$ and $R_{26}$ are Glu and $R_{25}$ and $R_{27}$ are Lys.

5. The ligand according to claim 1 wherein $R_{13}$ is CML and $R_{34}$ is Lys.

6. The ligand according to claim 1 wherein $R_{34}$ is Lys and $R_{39}$ is CML.

7. The ligand according to claim 1 which is cyclo(31–34) [D-Phe$^{11}$,CML$^{13,39}$,Glu$^{31}$,Lys$^{34}$]-Svg(11–40).

8. A tracer selective to CRFR2 which has the following amino acid sequence: Y-$R_{11}$-$R_{12}$-$R_{13}$-$R_{14}$-Arg-$R_{16}$-Nle-$R_{18}$-$R_{19}$-$R_{20}$-$R_{21}$-$R_{22}$-$R_{23}$-$R_{24}$-$R_{25}$-$R_{26}$-$R_{27}$-$R_{28}$-Gln-$R_{30}$-$R_{31}$-$R_{32}$-$R_{33}$-$R_{34}$-$R_{35}$-$R_{36}$-$R_{37}$-$R_{38}$-$R_{39}$-$R_{40}$-NH$_2$ wherein Y is radioiodinated tyrosine; $R_{11}$ is D-Phe, D-Leu, D-Tyr, D-Cpa, D-Nal, D-Pal, Phe, Leu, Tyr, Cpa, Nal or Pal; $R_{12}$ is His or Glu; $R_{13}$ is CML or Leu; $R_{14}$ is Leu or CML; $R_{16}$ is Glu, CML or Lys; $R_{18}$ is Leu, CML, Ile, Ala or Aib; $R_{19}$ is Glu, D-Glu or His; $R_{20}$ is Ile or Leu; $R_{21}$ is Ala, D-Ala, Aib, Thr, D-Thr, Glu or D-Glu; $R_{22}$ is Arg or Lys; $R_{23}$ is Gln or Ala or Aib; $R_{24}$ is Glu or Asp; $R_{25}$ is Lys or Gln; $R_{26}$ is Glu, Leu or CML; $R_{27}$ is Lys, Ala or Aib; $R_{28}$ is Gln or Glu; $R_{30}$ is Ala or Aib; $R_{31}$ is Glu or Gln; $R_{32}$ is Asn or Ser; $R_{33}$ is Asn or Aib; $R_{34}$ is Lys, Lys(Ac) or Orn; $R_{35}$ is Leu or Ile; $R_{36}$ is CML or Leu; $R_{37}$ is Leu or Nle; $R_{38}$ is Asp or Glu; $R_{39}$ is CML, Ile or Leu; $R_{40}$ is Ile, Ala, Gly, Val, Leu, Nle, Phe, Nva or Gln;

wherein a cyclizing bond may exist between the side chains of $R_{31}$ and $R_{34}$ so as to form a cyclo(31–34) structure, and wherein the N-terminus may be extended by up to 3 residues between Y and $R_{11}$.

9. A CRFR2 ligand, or a pharmaceutically acceptable salt thereof, which ligand exhibits CRF antagonist properties and binds selectively to CRFR2, said ligand having the formula: Y-$R_9$-$R_{10}$-$R_{11}$-$R_{12}$-$R_{13}$-$R_{14}$-Leu-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-Nle-$R_{39}$-$R_{40}$-$R_{41}$-NH$_2$ wherein Y is an acyl group having up to 15 carbon atoms; $R_9$ is Asp or des-$R_9$; $R_{10}$ is Leu or des-$R_{10}$; $R_{11}$ is Thr or Ser or des-$R_{11}$; $R_{12}$ is D-Phe, D-Leu, D-Tyr, D-Cpa, D-Nal, D-Pal, Phe, Leu, Tyr, Cpa, Nal or Pal; $R_{13}$ is His, Tyr or Glu; $R_{14}$ is CML or Leu; $R_{17}$ is Glu, CML, Asn or Lys; $R_{18}$ is Val, Nle, CML or Met; $R_{19}$ is Leu or Ile; $R_{20}$ is Glu, D-Glu, or His; $R_{22}$ is Ala, D-Ala, Aib, Asp, Thr, D-Thr, Glu or D-Glu; $R_{23}$ is Arg or Lys; $R_{24}$ is Ala, Aib or CML; $R_{25}$ is Glu or Asp; $R_{26}$ is Gln, Asn or Lys; $R_{27}$ is Leu or CML; $R_{28}$ is Ala, Lys, Aib or Arg; $R_{29}$ is Gln, Aib or Glu; $R_{30}$ is Gln or Glu; $R_{31}$ is Ala or Aib; $R_{32}$ is Glu or Gln; $R_{33}$ is Ser or Thr; $R_{34}$ is Asn or Aib; $R_{35}$ is Lys, Lys(Ac) or Orn; $R_{36}$ is Lys, Orn, Arg, Har, CML or Leu; $R_{37}$ is Leu, CML, or Tyr; $R_{39}$ is Glu, Aib or Asp; $R_{40}$ is CML, Ile, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln;

wherein a cyclizing bond may exist between the side chains of $R_{32}$ and $R_{35}$ so as to form a cyclo(32–35) structure.

10. The ligand of claim 9 wherein $R_{14}$ and $R_{40}$ are CML.

11. The ligand of claim 9 wherein a cyclizing bond connects the side chains of Glu$^{32}$ and $R_{35}$.

12. The ligand of claim 9 having the formula: cyclo (32–35)D-Phe-His-CML-Leu-Arg-Glu-Val-Leu-Glu-Nle-Ala-Arg-Ala-Glu-Gln-Leu-Ala-Gln-Gln-Ala-Glu-Ser-Asn-Lys-Lys-Leu-Nle-Glu-CML-Ile-NH$_2$.

13. The ligand of claim 9 having the formula: D-Phe-His-Leu-Leu-Arg-Glu-Val-Leu-Glu-Nle-Ala-Arg-Ala-Glu-Gln-Leu-Ala-Gln-Gln-Ala-Gln-Ser-Asn-Lys(Ac)-Lys-Leu-Nle-Glu-Ile-Ile-NH$_2$.

14. A CRFR2 ligand, or a pharmaceutically acceptable salt thereof, which ligand exhibits CRF antagonist properties and which binds selectively to CRFR2 comprising the following amino acid sequence: Y-$R_8$-$R_9$-$R_{10}$-$R_{11}$-His-$R_{13}$-Leu-Arg-Thr-Leu-Leu-$R_{19}$-Leu-Ala-Arg-Thr-Gln-Ser-Gln-Arg-Glu-Arg-Ala-$R_{31}$-Gln-Asn-$R_{34}$-Ile-$R_{36}$-Phe-$R_{38}$-$R_{39}$-Val-NH$_2$, wherein Y is H or an acyl group having up to 7 carbon atoms or radioiodinated tyrosine; $R_8$ is Asp or des-$R_8$; $R_9$ is Leu or des-$R_9$; $R_{10}$ is Thr, Ser or des-$R_{10}$; $R_{11}$ is D-Phe, D-Leu, D-Tyr, D-Cpa, D-Nal, D-Pal, Phe, Leu, Tyr, Cpa, Nal or Pal; $R_{13}$ is CML or Leu; $R_{19}$ is Glu or Ala; $R_{31}$ is Glu or Gln; $R_{34}$ is Lys, Lys(Ac) or Orn; $R_{36}$ is Ile, C$^\alpha$MeIle or CML; $R_{38}$ is Asp or Ala; $R_{39}$ is CML, Ser or Thr; wherein a cyclizing bond may exist between the side chains of Glu in the 31-position and $R_{34}$ so as to form a cyclo(31–34) structure.

15. The ligand according to claim 14 which is cyclo (31–34)[D-Phe$^{11}$,Lys$^{34}$]-Ucn(11–40).

16. The ligand according to claim 1 which is cyclo(31–34) [Y-D-Phe$^{11}$,His$^{12}$,CML$^{13,39}$,Nle$^{17}$,Glu$^{31}$,Lys$^{34}$]-Svg(8–40), wherein Y is H or an acyl group having up to 7 carbon atoms or radioiodinated tyrosine.

17. The ligand according to claim 1 which is cyclo(31–34) [Ac-D-Phe$^{11}$,His$^{12}$,CML$^{13,39}$,Nle$^{17}$,Glu$^{31}$,Lys$^{34}$]-Svg (8–40).

18. The ligand according to claim 1 which is cyclo(31–34) [Y-D-Phe$^{11}$,His$^{12}$,CML$^{13,39}$,Nle$^{17}$, Glu$^{31}$,Lys$^{34}$]-Svg (11–40), wherein Y is H or an acyl group having up to 7 carbon atoms or radioiodinated tyrosine.

19. A method for screening for antagonists for CRFR2 receptors which bind with high affinity to such receptors which method comprises:

carrying out a competitive binding assay with a CRFR2 receptor, a ligand according to claim 1, and a candidate antagonist, wherein said ligand is cyclo(31–34)[Ac-D-Phe$^{11}$,His$^{12}$, CML$^{13,39}$,Nle$^{17}$,Glu$^{31}$,Lys$^{34}$]-Svg(8–40) having a suitable label;

determining the ability of said candidate antagonist to displace said labeled ligand; and testing said candidate antagonist for its ability to antagonize an activity associated with CRF.

20. A method for screening for antagonists for CRFR2 receptors which bind with high affinity to such receptors which method comprises:

carrying out a competitive binding assay with a CRFR2 receptor, a ligand according to claim 14 having a suitable label, and a candidate antagonist;

determining the ability of said candidate antagonist to displace said labeled ligand; and testing said candidate antagonist for its ability to antagonize an activity associated with CRF.

* * * * *

UNITED STATES PATENT AND TRADEMARK OFFICE
CERTIFICATE OF CORRECTION

PATENT NO. : 7,141,546 B1
APPLICATION NO. : 10/210889
DATED : November 28, 2006
INVENTOR(S) : Jean E.F. Rivier et al.

It is certified that error appears in the above-identified patent and that said Letters Patent is hereby corrected as shown below:

Title Pg, Item (73) Assignee, delete "Biologicial" and insert --Biological-- therefor.

Signed and Sealed this

Twenty-seventh Day of March, 2007

JON W. DUDAS
*Director of the United States Patent and Trademark Office*